United States Patent
Wellershaus et al.

(10) Patent No.: US 6,790,193 B2
(45) Date of Patent: Sep. 14, 2004

(54) FOOT LIFTER ORTHESIS AND METHOD OF FORMATION

(75) Inventors: Ulf Wellershaus, Duderstadt (DE); Matthias Vollbrecht, Herzberg (DE)

(73) Assignee: Otto Bock Healthcare GmbH, Duderstadt (DE)

(*) Notice: Subject to any disclaimer, the term of this patent is extended or adjusted under 35 U.S.C. 154(b) by 193 days.

(21) Appl. No.: 09/815,765

(22) Filed: Mar. 23, 2001

(65) Prior Publication Data

US 2001/0027284 A1 Oct. 4, 2001

(30) Foreign Application Priority Data

Mar. 28, 2000 (DE) ..................................... 200 05 737 U

(51) Int. Cl.[7] .................................................. A61F 5/00
(52) U.S. Cl. ............................ 602/25; 602/27; 602/28; 128/882
(58) Field of Search ........................ 602/23, 25, 27–30, 602/65; 128/882

(56) References Cited

U.S. PATENT DOCUMENTS

| | | | |
|---|---|---|---|
| 2,847,991 A | * 8/1958 | Andrews | 602/28 |
| 3,916,886 A | 11/1975 | Rogers | |
| 4,013,070 A | * 3/1977 | Harroff | 602/21 |
| 4,408,600 A | * 10/1983 | Davis | 602/16 |
| 5,007,414 A | * 4/1991 | Sexton | 602/19 |
| 5,088,479 A | * 2/1992 | Detoro | 602/27 |
| 5,306,230 A | * 4/1994 | Bodine | 602/26 |
| 5,376,068 A | 12/1994 | Grifka | |
| 5,584,799 A | * 12/1996 | Gray | 602/5 |
| 5,695,453 A | * 12/1997 | Neal | 602/6 |
| 5,741,222 A | * 4/1998 | Fiore | 602/27 |
| 5,836,902 A | * 11/1998 | Gray | 602/5 |
| 5,853,380 A | 12/1998 | Miller | |
| 5,897,515 A | 4/1999 | Willner et al. | |
| 6,146,344 A | 11/2000 | Bader | |

FOREIGN PATENT DOCUMENTS

| | | | |
|---|---|---|---|
| DE | 39 28 627 | 9/1990 | |
| DE | 39 16 091 | 11/1990 | |
| EP | 0 567 783 B1 | 3/1993 | |
| GB | 2188550 A | * 10/1987 | ............. A61F/5/04 |

* cited by examiner

Primary Examiner—Nicholas D. Lucchesi
Assistant Examiner—Tam Nguyen
(74) Attorney, Agent, or Firm—Husch & Eppenberger, LLC; Robert C. Haldiman; David A. Chambers

(57) ABSTRACT

A foot lifter orthosis including a dorsal leg shell, extending over the rear foot, which can be fixed by a strapping means to the calf of the orthosis wearer and which has a forefoot shell section constructed in one piece which extends to a point below the foot sole region, wherein the leg shell exhibits a low resistance in dorsal foot bending and a high resistance compensating for the foot and shoe mass in plantar foot bending with at least one resilient inlay, which extends approximately parallel to and at a short distance from an edge of the leg shell from the calf region thereof to a point below the forefoot shell section. An associated method of formation is also disclosed.

14 Claims, 1 Drawing Sheet

FOOT LIFTER ORTHESIS AND METHOD OF FORMATION

BACKGROUND OF THE INVENTION

The invention concerns a foot lifter orthosis with a dorsal leg shell extending over the rear foot, which can be fixed by a strap or the like to the calf of the orthosis wearer and extends with a forefoot shell section constructed in one piece with it to a point below the foot sole region. A foot orthosis which is of similar construction with regard to the leg shell and designed as an ankle joint orthosis is described in EP 0 567 783 B1.

A significant problem with this type of foot lifter orthosis is the lack of adaptation of the foot of the orthosis wearer to the footwear worn by the orthosis wearer.

The present invention is directed to overcoming one or more of the problems set forth above.

SUMMARY OF THE INVENTION

In accordance with the present invention there is provided a foot lifter orthosis having a dorsal leg shell extending over the rear foot and made of plastic, which can fixed by a strapping means to the calf of the orthosis wearer and which has a forefoot shell section constructed in one piece which extends to a point below the foot sole region, wherein the leg shell exhibits a low resistance in dorsal foot bending and a high resistance compensating for the foot and shoe mass in plantar foot bending and is made of a soft, flexible plastic and two spring wire inlays, which extend approximately parallel to and at a short distance from the inner or outer edge of the leg shell from the calf region thereof to a point below the forefoot shell section and are embedded on the rear, lower side of the leg shell.

It is an aspect of the invention to improve the foot lifter orthosis described herein with respect to its adaptation to the foot of the orthosis wearer and to the footwear worn by the orthosis wearer.

It is an aspect of the invention to improve the foot lifter orthesis described herein with respect to its adaptation to the foot of the orthesis wearer and to the footwear worn by the orthesis wearer.

The foot lifter orthosis according to the invention achieves this object by virtue of its leg shell that exhibits a low resistance in dorsal foot bending and a high resistance compensating for the foot and shoe mass in plantar foot bending. It is made of a soft, flexible plastic, e.g. a low-density polyethylene or an EVA, in which two spring steel wire inlays are embedded on the rear or lower side of the leg shell. The two spring steel wire inlays extend approximately parallel to and at a short distance from the inner or outer edge of the leg shell from the calf region thereof to a point below the forefoot shell section.

The shape of the wire inlays determines the essential properties of the orthosis. It is appropriate if the wire inlays end approximately in the lower region of the heel bone.

To improve the comfort of wearing, it is advantageous if the wire inlays are almost completely surrounded by the plastic.

To save the shoe edge of footwear worn by the orthosis wearer, it is advantageous if a central rib is provided which is formed integrally in the rear heel region of the leg shell on the rear side thereof and which protrudes beyond the shoe edge thereof when the footwear worn.

A particularly suitable plastic is a low-density polyethylene LDPE 100 which is soft enough to naturally adapt to the foot of the orthosis wearer as well as the footwear worn by the orthosis wearer, without manual finishing. According to the invention, therefore, there is provided an autoadaptive foot orthosis having wire inlays to ensure a firm orthosis construction in the plantar region. Preferably a pre-bent spring steel wire with a diameter of 1.5 to 2 mm is used, which is fixed to distance holders before deep-drawing the leg shell in order to obtain complete surrounding by the plastic. Manufacture of the leg shell by injection molding is possible.

BRIEF DESCRIPTION OF THE DRAWING

Reference is now made to the drawing, which illustrates the best presently known mode of carrying out the invention and wherein similar reference characters indicate the same parts throughout the views.

DETAILED DESCRIPTION

Figure 1:
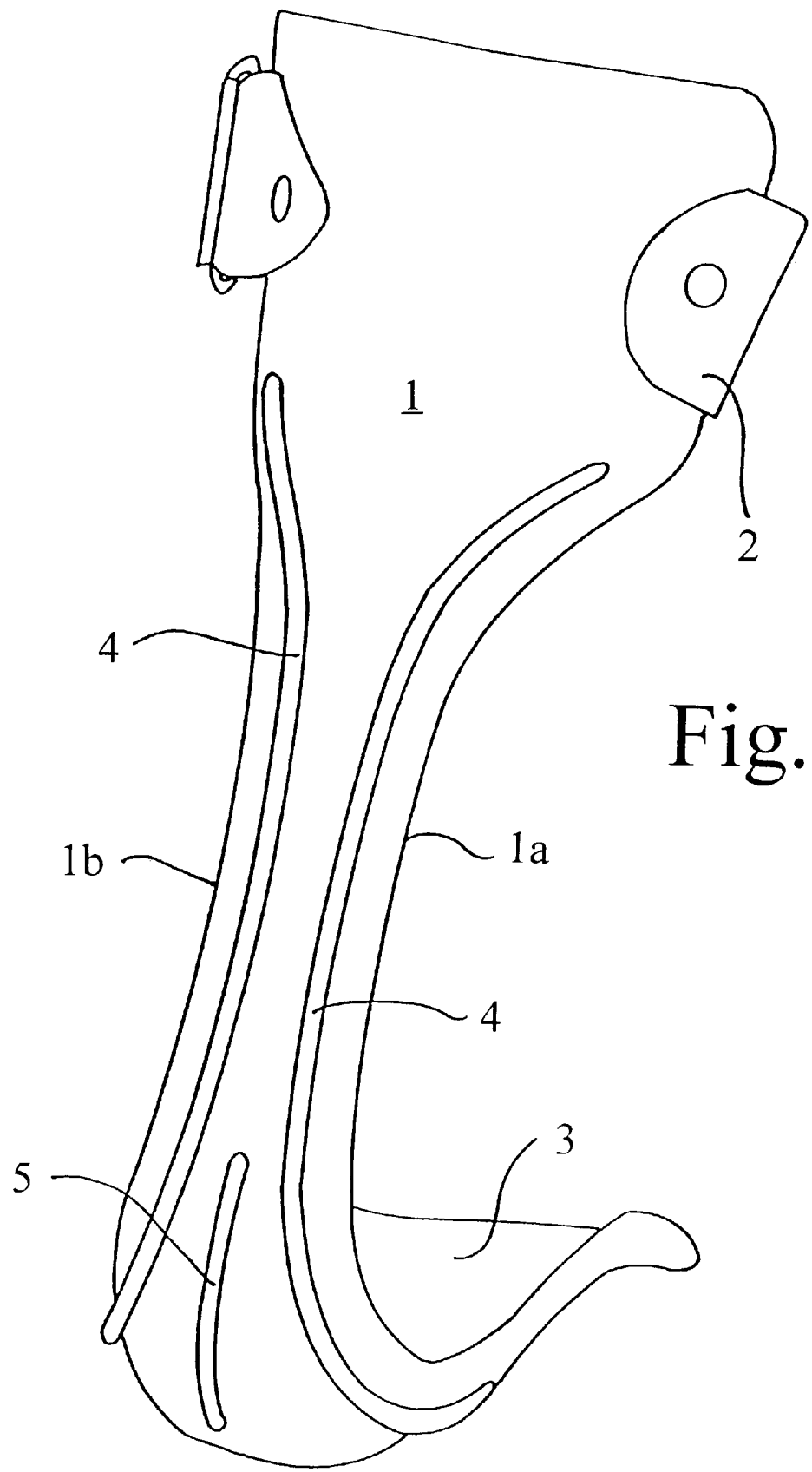
FIG. 1 is a rear view of a preferred embodiment of the foot lifter orthosis according to the present invention.

FIG. 1 shows, in a rear view, a foot lifter orthosis with a dorsal leg shell 1 extending over the rear foot and made of plastic, which can be fixed by a strap 2, such as a hook and pile type fastening, to the calf of the orthosis wearer.

The leg shell 1 extends to a point below the foot sole region with a forefoot shell section 3 constructed in one piece with it. The leg shell 1 includes two plastic-encased wire inlays 4 on its rear or lower side which extend, approximately parallel to and at a short distance from the inner edge 1a or outer edge 1b of the leg shell 1, from the calf region thereof to a point below the forefoot shell section 3, near the region of the heel bone.

Due to the arrangement of these wire inlays 4, which are preferably made of spring steel, it is possible to select a soft, flexible plastic for the leg shell 1, resulting in an autoadaptive foot lifter orthosis which exhibits a low resistance in dorsal foot bending and a high resistance compensating for the foot and shoe mass in plantar foot bending.

To prevent wear of the footwear, not shown in the drawing, worn by the orthosis wearer, there is provided a central rib 5 which is formed integrally in the rear heel region of the leg shell 1 and on the rear side thereof. When the footwear is put on, the central rib 5 protrudes beyond the shoe edge.

Other objects, features and advantages will be apparent to those skilled in the art. While a preferred embodiment of the present invention has been illustrated and described, this has been by way of illustration and the invention should not be limited except as required by the scope of the appended claims.

We claim:

1. A foot lifter orthesis comprising:
   a calf portion adapted to strap onto a dorsal side of a users lower leg, said calf portion hiring concave towards the users calf;
   a foot portion adapted to contact a bottom side of a users foot which said calf portion is attached to the users leg, said foot portion being concave towards the users foot over at least a heel portion of said orthosis;
   at least two stiffening elements fixed to said calf portion and extending into a heel portion;
   said concavity of said foot portion extending, at least as far forward as said stiffening elements, such that said concavity and said attachment of said calf portion to the user's leg resist plantar flexion of said foot portion, but does not resist dorsal flexion of said foot portion.

2. The orthosis of claim 1 wherein said calf portion and said foot portion are plastic.

3. The orthosis of claim 1 wherein said calf portion and said foot portion are integrally formed of a single piece of material.

4. The orthosis of claim 1 wherein said at least one stiffening element is a wire.

5. The orthosis of claim 1 wherein at least one stiffening element is a molded portion of plastic.

6. The orthosis of claim 1 further comprising a strap disposed to hold said calf portion against the users leg.

7. The orthosis of claim 1 further comprising a second stiffening element.

8. The orthosis of claim 2 wherein each of said foot ends of said stiffening elements are disposed bi-laterally to a user's heel.

9. The orthosis of claim 2 wherein said plastic is low density polyethylene.

10. The orthosis of claim 1 wherein said calf portion includes an EVA.

11. The orthosis of claim 4 wherein said wire is snap fit into a channel molded in said calf portion and said heel portion.

12. The orthosis of claim 1 further comprising an additional stiffening element extending substantially from a back of a users heel upwards towards a users calf.

13. The orthosis of claim 4 wherein said wire is spring steel of a diameter in range from about 1.5 mm to about 2.0 mm.

14. A method of producing a foot orthosis comprising:

molding plastic into a calf portion, a foot portion and a heel portion between said calf portion and said foot portion, at least said calf and heel portion being concave towards a user;

attaching two wires to said plastic alone each side of at least said calf portion; and extending said concavity of said heel portion at least as far forward as a farthest forward extension of said wires, such that said concavity and said wires resists plantar flexion of said foot portion more than said concavity resists dorsal flexion of said foot portion.

* * * * *

UNITED STATES PATENT AND TRADEMARK OFFICE
CERTIFICATE OF CORRECTION

PATENT NO. : 6,790,193 B2
DATED : September 14, 2004
INVENTOR(S) : Ulf Wellershaus et al.

It is certified that error appears in the above-identified patent and that said Letters Patent is hereby corrected as shown below:

Title page,
Item [54], Title, please change "ORTHESIS" to the word -- ORTHOSIS --

Column 2,
Line 53, please remove the word "lifter"
Line 53, please replace "orthesis" with the word -- orthosis --
Line 55, the word "hiring" should read -- being --
Line 58, please replace "which" with the word -- when --

Signed and Sealed this

First Day of February, 2005

JON W. DUDAS
*Director of the United States Patent and Trademark Office*